United States Patent [19]

Bitha et al.

[11] Patent Number: 4,716,157

[45] Date of Patent: Dec. 29, 1987

[54] HETEROCYCLIC-1,2-DIAMINE PLATINUM COMPLEXES

[75] Inventors: Panayota Bitha, Pomona; Ralph G. Child, Pearl River; Joseph J. Hlavka, Tuxedo Park; Yang-I Lin, Nanuet, all of N.Y.

[73] Assignee: American Cyanamid Company, Stamford, Conn.

[21] Appl. No.: 841,647

[22] Filed: Mar. 20, 1986

[51] Int. Cl.[4] .................... C07F 15/00; A61K 31/555
[52] U.S. Cl. .................................. 514/184; 514/188; 540/465; 540/541; 546/11; 548/402; 549/3; 549/206; 549/208
[58] Field of Search ............... 540/465, 541; 546/11; 548/402; 549/3, 208, 206; 514/184, 188

[56] References Cited

U.S. PATENT DOCUMENTS

| | | | |
|---|---|---|---|
| 4,115,418 | 9/1978 | Gale et al. | 556/137 |
| 4,410,544 | 10/1983 | Berg et al. | 556/137 X |
| 4,466,924 | 8/1984 | Verbeak et al. | 556/137 |
| 4,500,465 | 2/1985 | Amundsen et al. | 556/137 X |
| 4,614,811 | 9/1986 | Gandolfi | 556/137 |
| 4,661,516 | 4/1987 | Brown et al. | 550/137 X |

*Primary Examiner*—Richard L. Raymond
*Attorney, Agent, or Firm*—Edward A. Conroy, Jr.

[57] ABSTRACT

This disclosure describes platinum complexes of heterocyclic-1,2-diamines which possess the property of inhibiting the growth of tumors in mammals.

12 Claims, No Drawings

HETEROCYCLIC-1,2-DIAMINE PLATINUM COMPLEXES

SUMMARY OF THE INVENTION

This invention is concerned with new organic compounds of the formulae I and II:

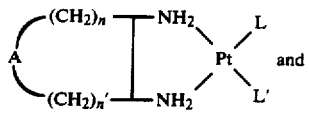

Formula I

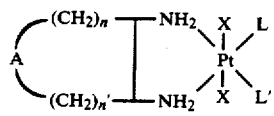

Formula II wherein A is selected from the group consisting of O, $SO_2$, N[alkyl($C_1$-$C_5$)] and

n and n' are integers 1-3; L and L' are selected from the group consisting of halide, nitrate, sulfate and a monobasic carboxylate such as acetate or hydroxy acetate, L and L' taken together are ascorbate, a dibasic carboxylate selected from the group consisting of

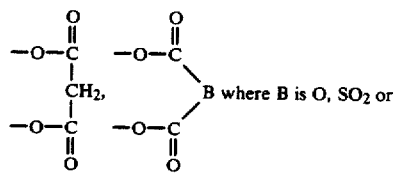

B where B is O, $SO_2$ or N—[alkyl($C_1$-$C_5$)],

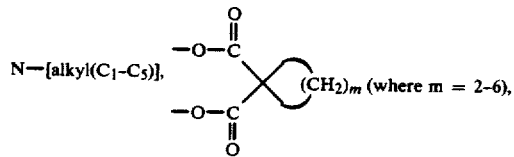

($CH_2$)$_m$ (where m = 2-6),

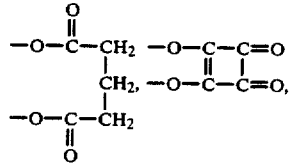

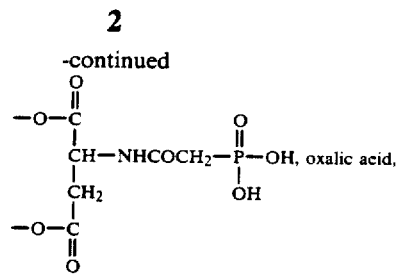

methylmalonic acid, succinic acid and tartronic acid, L and L' taken together maybe a tribasic carboxylate selected from the group consisting of

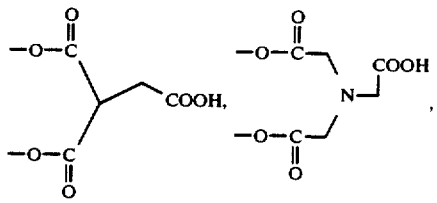

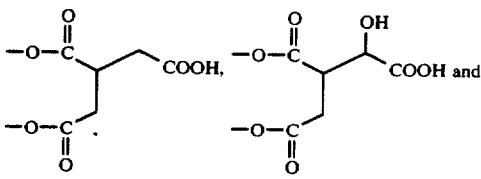

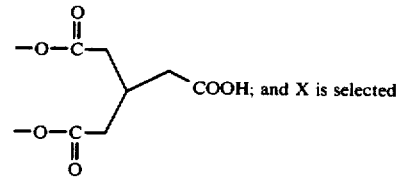

COOH; and X is selected from the group consisting of halogen and hydroxy.

This invention is further concerned with compounds of the formula III:

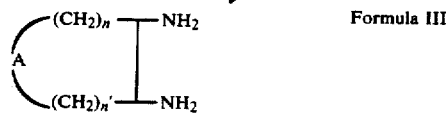

Formula III wherein A is selected from the group consisting of O, $SO_2$, N-[alkyl($C_1$-$C_5$)] and

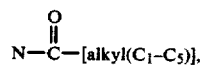

and n and n' are integers 1-3, with the proviso that when A is O or $SO_2$, n and n' may not each be one.

The compounds of this invention may be prepared as follows.

Flowchart A

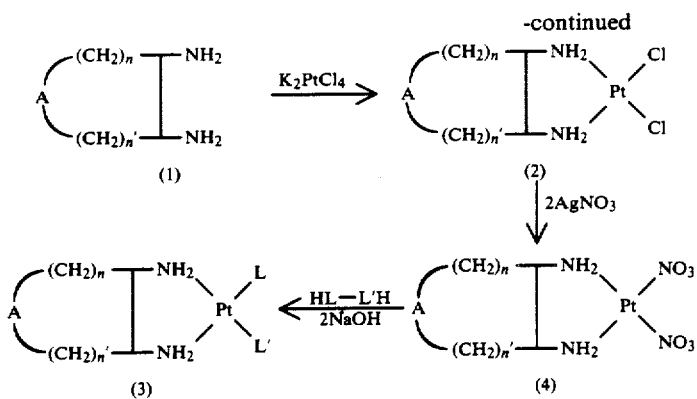

-continued

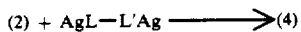

Flowchart B (2) + AgL—L'Ag ⟶ (4)

Flowchart C

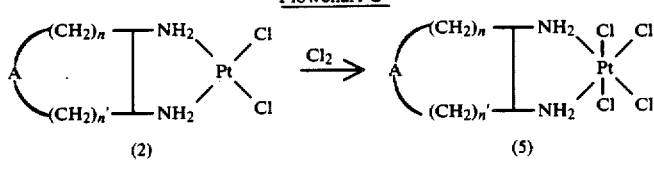

Flowchart D

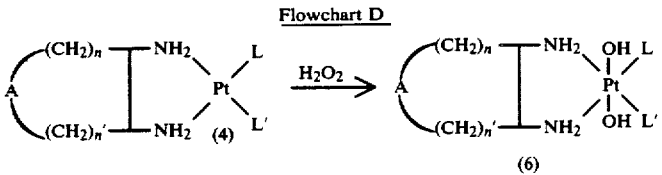

According to Flowchart A, the diamino compound (1) is reacted with potassium tetrachloroplatinate to give the dichloro platinum complex (2) which is then reacted with silver nitrate to give the dinitrato platinum complex (3). Reaction of the dinitrato complex (3) with a dibasic organic acid HL-L'H in the presence of two equivalents of sodium hydroxide gives the product (4).

Alternatively (Flowchart B), the dichloro platinum complex (2) may be reacted with the disilver salt of a dibasic organic acid to give the product (4).

According to Flowcharts C and D dichloroplatinum derivative 2 may be reacted with chlorine to give 5 and 4 may be reacted with hydrogen peroxide to give 6.

The novel complexed compounds of this invention possess the property of inhibiting the growth of transplanted tumors in mammals as established by the following tests.

Lymphocytic Leukemia P388 Test

The animals used were BDF/1 mice, all of one sex, weighing a minimum of 18 g and all within a 3 g weight range. There were 5 or 6 animals per test group. The tumor transplant was by intraperitoneal injection of 0.5 ml of dilute ascitic fluid containing $10^6$ cells of lymphocytic leukemia P388. The test compounds were administered intraperitoneally on days 1, 5 and 9 relative to tumor inoculation, at various doses. The animals were weighed and the survivors recorded on a regular basis for 30 days. The median survival time and the ratio of survival time for treated (T)/control (C) animals were calculated. The positive control compound was Cisplatin. The results of this test with representative compounds of this invention appear in Table I.

TABLE I

| Lymphocytic Leukemia P388 Test | | | |
|---|---|---|---|
| Compound | Dose (mg/kg) | Median Survival (Days) | T/C × 100 (%) |
| Dichloro(trans-tetrahydro-3,4-furandiamine-N̲,N̲')platinum | 25 | 25.5 | 232 |
|  | 12.5 | 22.5 | 205 |
|  | 6.2 | 20 | 182 |
|  | 3.1 | 17 | 155 |
|  | 1.5 | 16 | 145 |
| Control | — | 11 | — |
| Cisplatin | 4 | >30 | >273 |
|  | 2 | 23.5 | 214 |
|  | 1 | 20.5 | 186 |
| (1,1-cyclobutanedicarboxylato-(2-)-0¹,0¹¹((racemic)tetrahydro-3,4-furandiamine-N̲,N̲')—platinum | 100 | 20 | 154 |
|  | 50 | 19.5 | 150 |
|  | 25 | 14 | 108 |
|  | 12.5 | 13 | 100 |
| Control | — | 13 | — |
| Cisplatin | 4 | >30 | >231 |
|  | 2 | 24 | 185 |
|  | 1 | 20 | 154 |
| [propanedioato-(2-)-0¹,0³](trans-(racemic)(tetrahydro-3,4-furandiamine-N̲,N̲')platinum | 100 | 23 | 184 |
|  | 50 | 19 | 152 |
|  | 25 | 16.5 | 132 |
|  | 12.5 | 17.5 | 140 |
|  | 6.2 | 15.5 | 124 |
|  | 3.1 | 13 | 104 |
|  | 1.5 | 15.5 | 124 |
| Control | — | 12.5 | — |
| Cisplatin | 4 | >30 | >240 |
|  | 2 | 25 | 200 |
|  | 1 | 20.5 | 164 |
| Tetrachloro(trans-(racemic)-tetrahydro-3,4-furandiamine-N̲,N̲']platinum | 50 | >30 | >240 |
|  | 25 | 25.5 | 204 |
|  | 12.5 | 20 | 160 |
|  | 6.2 | 17.5 | 140 |
|  | 3.1 | 16 | 128 |
| Control | — | 12.5 | — |

TABLE I-continued

Lymphocytic Leukemia P388 Test

| Compound | Dose (mg/kg) | Median Survival (Days) | T/C × 100 (%) |
|---|---|---|---|
| Cisplatin | 4 | >30 | >240 |
|  | 2 | 25 | 200 |
|  | 1 | 20.5 | 164 |
| [L-threo-3-hexulosonato(2-)-$C^2$,-$O^5$,gamma-lactone](trans-tetrahydro-3,4-furandiamine-$\underline{N},\underline{N}'$)—platinum | 100 | 29.5 | 295 |
|  | 50 | 27.5 | 275 |
|  | 25 | 22 | 220 |
|  | 12.5 | 18 | 180 |
|  | 6.2 | 19 | 190 |
|  | 3.1 | 17 | 170 |
|  | 1.5 | 14 | 140 |
| Control | — | 10 | — |
| Cisplatin | 4 | >30 | >300 |
|  | 2 | 22 | 220 |
|  | 1 | 17 | 170 |
| Bis[hydroxyacetato(1-)-$O^1$](trans-tetrahydro-3,4-furandiamine-$\underline{N},\underline{N}'$)platinum | 50 | 24 | 218 |
|  | 25 | 24.5 | 223 |
|  | 12.5 | 21.5 | 195 |
|  | 6.2 | 18 | 164 |
|  | 3.1 | 17 | 155 |
|  | 1.5 | 14.5 | 132 |
| Control | — | 11 | — |
| Cisplatin | 4 | >30 | >273 |
|  | 2 | 23.5 | 214 |
|  | 1 | 20.5 | 186 |

Melanotic Melanoma B16

The animals used were C57BC/6 mice, all of the same sex, weighing a minimum of 17 g and all within a 3 g weight range. There were 10 animals per test group. A 1 g portion of melanotic melanoma $B_{16}$ tumor was homogenized in 10 ml of cold balanced salt solution and a 0.5 ml aliquot of the homogenate was implanted intraperitoneally into each of the test mice. The test compounds were administered intraperitoneally on days 1 through 9, relative to tumor inoculation, at various doses. The animals were weighed and survivors recorded on a regular basis for 60 days. The median survival time for treated (T)/control (C) animals were calculated. The positive control compound was Cisplatin. The results of this test appear in Table II.

TABLE II

Melanotic Melanoma B16 Test

| Compound | Dose (mg/kg) | Median Survival (Days) | T/C × 100 (%) |
|---|---|---|---|
| Dichloro((trans)tetrahydro-3,4-furandiamine-$\underline{N},\underline{N}'$)platinum | 12.5 | 32.5 | 135 |
|  | 6.2 | 31.5 | 132 |
|  | 3.1 | 30 | 125 |
|  | 1.6 | 27.5 | 115 |
|  | 0.8 | 25.5 | 106 |
| Control | — | 24 | — |
| Cisplatin | 0.4 | 31 | 129 |
|  | 0.2 | 34 | 142 |
|  | 0.1 | 28 | 117 |
|  | 0.05 | 25.5 | 106 |
| [1,1-cyclobutanedicarboxylato-(2-)-0,$0^1$]((racemic)tetrahydro-3,4-furandiamine-$\underline{N},\underline{N}'$)platinum | 100 | 36 | 163 |
|  | 50 | 35.5 | 161 |
|  | 25 | 30 | 136 |
|  | 12 | 29 | 131 |
|  | 6 | 25.5 | 116 |
| Control | — | 22 | — |
| Cisplatin | 0.4 | 31 | 140 |
|  | 0.2 | 30 | 136 |
|  | 0.1 | 27.5 | 125 |
|  | 0.05 | 25.5 | 116 |
| Tetrachloro (trans-(racemic)-tetrahydro-3,4-furandiamine $\underline{N},\underline{N}'$)platinum | 12 | 22 | 88 |
|  | 6 | 32 | 128 |
|  | 3 | 28 | 112 |
|  | 1.5 | 27.5 | 110 |
| Control | — | 25 | — |
| Cisplatin | 0.4 | 30 | 120 |

TABLE II-continued

Melanotic Melanoma B16 Test

| Compound | Dose (mg/kg) | Median Survival (Days) | T/C × 100 (%) |
|---|---|---|---|
|  | 0.2 | 27.5 | 110 |
|  | 0.1 | 27.5 | 110 |
|  | 0.05 | 27.5 | 110 |
| [L-threo-3-hexulosonato-(2-)-$C^2$, $O^5$ gamma-lacetone]trans-tetrahydro-3,4-furandiamine-$\underline{N},\underline{N}'$)-platinum | 100 | 23.5 | 94 |
|  | 50 | 32.5 | 130 |
|  | 25 | 29 | 116 |
|  | 12 | 27 | 108 |
|  | 6 | 25 | 100 |
| Control | — | 25 | — |
| Cisplatin | 0.4 | 30 | 120 |
|  | 0.2 | 27.5 | 110 |
|  | 0.1 | 27.5 | 110 |
|  | 0.05 | 27.5 | 110 |
| Bis[hydroxyacetato(1-)$0^1$](trans-tetrahydro-3,4-fuandiamine-$\underline{N},\underline{N}'$)platinum | 25 | | |
|  | 12.5 | | |
|  | 6.2 | | |
|  | 3.1 | | |
|  | 1.6 | | |
| Control | — | | — |
| Cisplatin | 0.4 | | |
|  | 0.2 | | |
|  | 0.1 | | |
|  | 0.05 | | |

Colon 26 Adenocarcinoma Test

The animals used were Balb/C mice all of one sex, weighing a minimum of 17 g and all within a 3 g weight range. There were 5 or 6 mice per test group with three groups of 5 or 6 animals used as untreated controls for each test. The tumor implant was by intraperitoneal (or subcutaneous) injection of 0.5 ml of a 2% Colon 26 tumor brei in Eagle's MEM medium containing antibiotics. The test compounds were administered intraperitoneally on days 1, 5 and 9 (relative to tumor implant doses). The mice were weighed and deaths recorded on a regular basis for 30 days. The median survival times and the ratio of survival time for treated (T)/control (C) animals were calculated. The positive control compound was Cisplatin. The results of this test on representative compounds of this invention appear in Table III.

TABLE III

Colon 26 Adenocarcinoma Test

| Compound | Dose (mg/kg) | Median Survival (Days) | T/C × 100 (%) |
|---|---|---|---|
| Dichloro(trans-tetrahydro-3,4-furandiamine-$\underline{N},\underline{N}'$)platinum | 25 | 30.5 | 153 |
|  | 12.5 | 35 | 175 |
|  | 6.2 | 26.5 | 133 |
|  | 3.1 | 25.5 | 128 |
| Control | — | 20 | — |
| Cisplatin | 1 | 36 | 180 |
|  | 0.5 | 28 | 140 |
|  | 0.25 | 27.5 | 138 |
|  | 0.125 | 20.5 | 103 |
| Tetrachloro(trans(racemic)-tetrachloro-3,4-furandiamine-$\underline{N},\underline{N}'$)platinum | 50 | | |
|  | 25 | | |
|  | 12 | | |
|  | 6 | | |
| Control | — | | — |
| Cisplatin | 1 | | |
|  | 0.5 | | |
|  | 0.25 | | |
|  | 0.125 | | |
| [L-threo-3-hexulosonato(2-)-$C^2$, $O^5$ gamma-lactone](trans-tetrahydro-3,4-furandiamine-$\underline{N},\underline{N}'$)-platinum | 100 | 30.5 | 156 |
|  | 50 | 22.5 | 115 |
|  | 25 | 26.5 | 136 |
|  | 12 | 22 | 113 |
| Control | — | 19.5 | — |
| Cisplatin | 1 | 31.5 | 162 |

TABLE III-continued

Colon 26 Adenocarcinoma Test

| Compound | Dose (mg/kg) | Median Survival (Days) | T/C × 100 (%) |
|---|---|---|---|
| | 0.5 | 28 | 144 |
| | 0.25 | 21 | 108 |
| | 0.125 | 21 | 108 |
| Bis[hydroxyacetato(1-)-$O^1$]-(trans-tetrahydro-3,4-furandiamine-$\underline{N},\underline{N}'$)platinum | 50 25 12.5 6.2 | | |
| Control | — | | — |
| Cisplatin | 1 0.5 0.25 0.125 | | |

Lymphocytic Leukemia L1210 Test

The animals used $BDF_1$ of $CD_2F_1$ mice, all of one sex, weighing a minimum of 17 g and all within a 3 g weight range. There were 6 mice in each test group and 18 in control groups. The tumor transplant was by intraperitoneal injection of 0.5 ml of lymphocytic leukemia L1210 at a concentration of $10^5$ cells per mouse. The test compounds were administered on days 1, 5 and 9 (relative to tumor inoculaion) at various doses. The mice were weighed and survivors recorded on a regular basis for 30 days. The median survival time and the ratio of survival time for treated (T)/control (C) animals were calculated. The positive control compound was Cisplatin given intraperitoneally at the indicated doses. The results of this test on representative compounds of this invention appear in Table IV.

TABLE IV

Lymphocytic Leukemia L1210 Test

| Compound | Dose (mg/kg) | Median Survival (Days) | T/C × 100 (%) |
|---|---|---|---|
| Dichloro((trans)tetrahydro-3,4-furandiamine-$\underline{N},\underline{N}'$)platinum | 25 12.5 6.2 3.1 | 15 13 12 10 | 150 130 120 100 |
| Control | — | 10 | — |
| Cisplatin | 4 2 1 | 16 12 10.5 | 160 120 105 |
| [1,1-cyclobutanedicarboxylato-(2-)-0,$O^1$]((racemic)tetrahydro-3,4-furanadiamine-$\underline{N},\underline{N}'$)-platinum | 100 50 25 12.5 6.2 | 7 10 9 9 9 | 78 111 100 100 100 |
| Control | — | 9 | — |
| Cisplatin | 4 2 1 | 18 11 10 | 200 122 111 |
| Tetrachloro(trans-(racemic)-tetrahydro-3,4-furandiamine-$\underline{N},\underline{N}'$)platinum | 50 25 12.5 | 16 14 13 | 160 140 130 |
| Control | — | 10 | — |
| Cisplatin | 4 2 1 | 16 12 10.5 | 160 120 105 |
| [L-thero-3-hexulosonato(2-)-$C^2$, $O^5$, gamma-lactone](trans-tetrahydro-3,4-furandiamine-$\underline{N},\underline{N}'$)-platinum | 100 50 25 | 13.5 12 10 | 135 120 100 |
| Control | — | 10 | — |
| Cisplatin | 4 2 1 | 16 12 10.5 | 160 120 105 |
| Bis[hydroxyacetato(1-)-$O^1$](trans-tetrahydro-3,4-furandiamine-$\underline{N},\underline{N}'$)platinum | 50 25 12.5 6.2 | 16 13 11 10 | 178 144 122 111 |
| Control | — | 9 | — |
| Cisplatin | 4 2 1 | 15 13 11 | 127 144 122 |

This aspect of the invention includes novel compositions of matter and the method of inducing the regression and/or palliation of leukemia and related cancers in mammals using the novel compounds of this invention when administered in amounts ranging from about 1 mg to about 1.2 g per square meter of body surface area per day. The interrelationship of dosages for animals of various sizes and species and humans (based on mg/m$^2$ of surface area) is described by Freireich, E. J., et al., Quantitative Comparison of Toxicity of Anticancer Agents in Mouse, Rat, Hamster, Dog, Monkey and Man. Cancer Chemother, Rep. 50, No. 4, 219–244, May 1966. A preferred dosage regimen for optimum results would be from about 3 mg/m$^2$/day to about 200 mg/m$^2$/day, and such dosage units are employed that a total of from about 5 mg to about 360 mg of the active compound for a subject of about 70 kg of body weight are administered in a 24 hour period. This dosage regimen may be adjusted to provide the optimum therapeutic response. For example, serveral divided doses may be administered daily or the dose may be proportionally reduced as indicated by the exigencies of the therapeutic situation. The active compound may be administered by the intravenous, intramuscular or subcutaneous routes.

The active compounds may be administered parenterally. Solutions or dispersions of the active compound can be prepared in water, suitably mixed with a surfactant such as hydroxypropylcellulose. Dispersions can also be prepared in glycerol, liquid polyethylene glycols, and mixtures thereof in oils. Under ordinary conditions of storage and use these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved aganist the contaminating action of microorganisms such as bacteria and fungi. The carrier can be a solvent or dispersion medium containing, for example, water, ethanol, polyol (e.g. glycerol, propylene glycol, liquid polyethylene glycol), suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be obtained by the use in the compositions of agents which delay adsorption, for example, aluminum monostearate and gelatin. Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatable with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subject to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from about 2 mg to about 2 g, with from about 5 to about 360 mg being preferred. Expressed in proportions, the active compound is generally present in from about 2 to about 100 mg/ml of carrier. In the case of compositions containing supplementary active ingredients, the dosages are determined by reference to the usual dose and manner of administration of the said ingredients.

Regression and palliation of cancers are attained, for example, using intraperitoneal administration. A single intravenous dosage or repeated daily dosages can be administered. Daily dosages up to about 5 or 10 days are often sufficient. It is also possible to dispense one daily dosage or one dose on alternate or less frequent days. As can be seen from the dosage regimens, the amount of principal active ingredient administered is a sufficient amount to aid regression and palliation of the leukemia or the like, in the absence of excessive deleterious side effects of the cytotoxic nature to the host harboring the cancer. As used herein, cancer disease means blood malignancies such as leukemia, as well as other solid and nonsolid malignancies such as the melanocarcinomas, lung carcinomas and mammary tumors. By regression and palliation is meant arresting or retarding the growth of the tumor or other manifestation of the disease compared to the course of the disease in the absence of treatment.

This invention will be described in greater detail in conjuction with the following non-limiting specific examples.

EXAMPLE 1

Dichloro(trans-tetrahydro-3,4-furandiamine-N,N')platinum

A 54.3 g portion of mercuric chloride was added to a solution of 27.6 g of sodium nitrite in water. To this solution was added 14 g of 2,5-dihydrofuran. The mixture was stirred overnight, then the solid was collected, washed with water, ethanol and ether and dried, giving 38.3 g of chloro(trans-tetrahydro-4-nitro-3-furanyl)mercury.

A 17.61 g portion of chloro(trans-tetrahydro-4-nitro-3-furanyl)mercury was slurried in a mixture of 1 liter of methylene chloride and 400 ml of water. A 10 ml portion of 5N sodium hydroxide was added with vigorous stirring which was continued for 20 minutes. The mixture was then acidified to pH 3.0 with concentrated hydrochloric acid and filtered. The methylene chloride phase of the filtrate was separated and evaporated to dryness, giving 4.43 g of 2,5-dihydro-3-nitrofuran as an oil.

A solution of 2.7 g of 2,5-dihydro-3-nitrofuran, 6.1 ml of concentrated ammonium hydroxide and 100 ml of tetrahydrofuran was stirred in a pressure bottle at 45° C. in an oil bath for 24 hours, then cooled in an ice bath and evaporated to dryness, giving 2.89 g. of trans-(racemic)-tetrahydro-4-nitro-3-furanamine.

A mixture of 2.85 g of trans-(racemic)-tetrahydro-4-nitro-3-furanamine, 850 mg of 10% palladium on carbon, 40 ml of ethanol and 15 ml of water was reduced in a Parr shaker overnight. The mixture was filtered and the filtrate evaporated, giving 2.2 g of trans-(racemic)-tetrahydro-3,4-furandiamine as an oil.

A 2.2 g portion of trans-(racemic)-tetrahydro-3,4-furandiamine was dissolved in 20 ml of water, filtered and the filtrate was added a solution of 8.95 g of potassium tetrachloroplatinate in 45 ml of water. This mixture was stirred overnight, then the precipitate was collected, washed with water and ether and dried, giving 4.44 g of the desired product.

EXAMPLE 2

[1,1-Cyclobutanedicarboxylato(2-)-O,O$^1$](racemic) (tetrahydro-3,4-furandiamine-N,N')platinum A suspension of 2.32 g of dichloro(trans-tetrahydro-3,4-furandiamine-N-N')platinum, 2.25 g. of the disilver salt of 1,1-cyclobutanedicarboxylic acid and 210 ml of water was stirred vigorously overnight in the dark and then filtered. The filtrate was concentrated to 30 ml. and again filtered. This filtrate was concentrated to 20 ml., then refrigerated for 1.5 hours and the solid collected, washed with water and ethanol and dried, giving 688 mg of the desired product.

EXAMPLE 3

[Propanedioato-(2-)-O$^1$, O$^3$](trans-(racemic)tetrahydro-3,4-furandiamine-N,N')platinum A suspension of 1.47 g of dichloro-(trans-tetrahydro-3,4-furandiamine-N,N')platinum, 1.27 g of the disilver salt of propanedioic acid and 140 ml of water was stirred overnight in the dark and then filtered. The filtrate was evaporated to dryness, giving 995 mg of the desired product.

EXAMPLE 4

Tetrachloro(trans-(racemic-tetrahydro-3,4-furandiamine-N,N')platinum

A 1.20 g portion of dichloro(trans-tetrahydro-3,4-furandianine-N,N')platinum was slurried in 40 ml of 0.5N hydrochloric acid and heated in an oil bath at 100° C. for 2 hours while chlorine gas was bubbled through the solution. Nitrogen was then bubbled through the reaction mixture. The solid was collected, washed with water and methanol and dried, giving 335 mg of the desired product.

EXAMPLE 5

[L-threo-3-Hexulosonato(2-)—C$^2$, O$^5$ gammalacetone](trans-tetrahydro-3,4-furandiamine-N,N')platinum A solution of 1.36 g of silver nitrate in 10 ml of water was added to a suspension of 1.47 g of dichloro(trans-tetrahydro-3,4-furandiamine-N,N'-)platinum in 50 ml of water. The mixture was stirred in the dark 3.5 hours and then filtered. To the filtrate, containing trans-dinitro(-tetrahydro-3,4-furandiamine-N,N')platinum, was added a solution of 1.58 g of sodium ascorbate in 10 ml of water. The solution was filtered, the filtrate stirred in the dark overnight and then evaporated to about 10 ml. The suspension was filtered, the filtrate diluted to 20 ml with water and poured into 200 ml of ethanol. The solid was collected, washed with ethanol and ether and dried, giving 1.2 g of the desired product.

EXAMPLE 6

Bis[hydroxyacetato(1-)-O$^1$]—(trans-tetrahydro-3,4-furandimaine-N,N')platinum

A suspension of 1.47 g of dichloro(trans-tetrahydro-3,4-furandiamine-N,N')platinum, 1.46 g of the silver salt of hydroxyacetic acid and 140 ml of water was stirred in the dark overnight and then filtered. The filtrate was evaporated to dryness, the residue slurried in methanol, diluted with ether and the solid collected and dried, giving 1.46 g of the desired product.

EXAMPLE 7

Dichloro(trans-tetrahydro-3,4-thiophenediamine 1,1-dioxide-N,N')platinum

A 2.23 g portion of trans-tetrahydro-3,4-thiophenediamine 1,1-dioxide, dihydrochloride (J.C.S. Perkin Trans. 1 (22), 2866–2872(1972) is dissolved in 10 ml of 1N hydroxide. A solution of 4.15 g of potassium tetrachlorophatinate in 25 ml of water is added and the mixture is stirred overnight. The precipitate is collected, washed with water, ether and dried, giving 3.5 g of the desired product.

EXAMPLE 8

[1,1-Cyclobutanedicarboxylato-(2-)-O,O$^1$](trans-tetrahydro-3,4-thiophenediamine 1,1-dioxide-N,N')platinum A suspension of 4.16 g of dichloro(trans-tetrahydro-3,4-thiophenediamine 1,1-dioxide-N,N')-platinum, 3.58 g of the disilver salt of 1,1-cyclobutanedicarboxylic acid and 300 ml of water is stirred vigorously overnight in the dark and then filtered. The filtrate is concentrated to 60 ml and again filtered. This filtrate is concentrated to 20 ml and then refrigerated for 1.5 hours. The solid is collected, washed with water and ethanol and dried, giving 2.1 g of the desired product.

EXAMPLE 9

Tetrahydro-2H-pyran-3,4-diamine

A 50 g portion of 2-deoxy-6-ribose was dissolved in 1.21 liters of methanol, the solution cooled in an ice bath to 5° C. and 15 g of sodium borohydride was added slowly over a period of 1 hour. The reaction was stirred in the ice bath for 4 hours, then the pH was adjusted to 3.5 with an anion exchange resin [DOWEX ®50X8(H+ form)]. The resin was removed by filtration and washed with methanol. The combined filtrate and wash was evaporated to an oily residue which when dried gave 50.4 g of 2-deoxy-D-erythropentital.

A 5.07 g portion of 2-deoxy-D-erythro-pentitol was codistilled with two 50 ml portions of pyridine, then dissolved in 50 ml of dry pyridine, cooled in an ice bath and 9 ml of benzoyl chloride was added slowly using an addition funnel. The reaction mixture was stirred in the ice bath for 2 hours and then refrigerated overnight. A 10 ml portion of water was added to the solution which was then stored at room temperature for 30 minutes and evaporated to dryness. A 200 ml portion of ethyl acetate was added and the solution was washed with three 50 ml portions of water. The ethyl acetate phase was dried over magnesium sulfate and evaporated to dryness. The residue was slurried in ether/petroleum ether and filtered. The product crystallized from ethanol, giving 5.23 g of 2-deoxy-D-erythro-pentital, 1,5-dibenzoate.

A 10.3 g portion of 2-deoxy-D-erythro-pentital, 1,5-dibenzoate was dissolved in cold pyridine and 0.2 ml of methanesulfonyl chloride was added dropwise through an addition funnel. The mixture was stirred in an ice bath for 3 hours, then the pyridine hydrochloride was removed by filtration and the filtrate poured into 100 ml of ice containing 60 ml of concentrated hydrochloric acid. The gummy precipitate was extracted with three 100 ml portions of chloroform. The combined chloroform extracts were washed with two 75 ml portions of water, two 75 ml portions of saturated sodium bicarbonate solution and two 75 ml portions of water, dried over magnesium sulfate and evaporated, giving 15.3 g of 2-deoxy-D-erythro-pentital, 1,5-dibenzoate, 3.4-dimethanesulfonate.

A solution of 15.02 g of 2-deoxy-D=erythro-pentitol, 1,5-dibenzeate, 3,4-dimethanesulfonate in 80 ml of dimethylformamide was mixed with 11.6 g of sodium azide and heated at 110° C. in an oil bath overnight. The suspension was cooled to room temperature, 150 ml of water added and the solution extracted with three 150 ml portions of ether. The ether extracts were combined, washed with three 100 ml portions of water, 70 ml of saturated sodium chloride solution, two 70 ml portions of 1% sodium bicarbonate solution and 100 ml of water, dried over magnesium sulfate and evaporated to dryness, giving 10.14 g of 3,4-diazido-2,3,4-trideoxy-D-erythro-pentitol, dibenzeate as an oil.

A 10 g portion of 3,4-diazido-2,3,4-trideoxy-D-erythro-pentitol, dibenzeate was dissolved in 35 ml of ethanol, a 1.8 g portion of platinum dioxide added and the mixture reduced in a Parr shaker overnight. The catalyst was removed by filtration and the filtrate evaporated to dryness, giving 4.36 g of 3,4-diamino-2,3,4-trideoxy-D-erythro-pentitol, 1,5-dibenzerate.

An 8.36 g portion of 3,4-diamino-2,3,4-trideoxy-D-erythro-pentitol, 1,5-dibenzerate.

An 8.36 g portion of 3,4-diamino-2,3,4-trideoxy-D-erythro-pentitol, 1,5-dibenzoate was dissolved in 280 ml of 0.1M sodium methoxide in methanol and the solution was stored overnight, then acidified to pH 6.0 with acetic acid and evaporated to dryness. The residue was titrated with chloroform, filtered and the filtrate evaporated to dryness, giving 1.2 g of 3,4-diamino-2,3,4-trideoxy-D-erythro-pentitol as an oil.

A solution of 0.94 g of 3,4-diamino-2,3,4-trideoxy-D-erythro-pentitol in 30 ml of 48% hydrobromic acid is refluxed at 140° C. for 24 hours and then evaporated to dryness.

The residue is dissolved in 2 ml of 48% hydrobromic acid and refrigerated for 48 hours. The crystalline solid is collected, washed with ethanol and dried, giving 857 mg of tetrahydro-2H-pyran-3,4-diamine, dihydrobromide.

The product is converted to the free amine by passing it through a column packed with ion exchange resin [DOWEX ®—X4(OH⁻ form)].

EXAMPLE 10

Dichloro(cis-tetrahydro-2H-pyran-3,4-diamine-N,N')Platinum

A solution of 580 mg of tetrahydro-2H-pyran-3,4-diamine in 10 ml of water is added to a solution of 2.07 g of potassium tetrachloroxoplatinate in 40 ml of water. The resulting suspension is stirred overnight, the solid collected, washed with two 10 ml portions of water and dried, giving 1.7 g of the desired product.

EXAMPLE 11

[1,1-cyclobutanedicarboxylato-(2-)-O,O¹](cis-tetrahydro-2H-pyran-3,4diamine-N,N')platinum A suspension of 3.82 g of dichloro(cis-tetrahydro-2H-pyran-3,4-diamine-N,N')platinum, 3.58 g of the disilver salt of 1,1-cyclobutanedicarboxylic acid and 300 ml of water is stirred vigorously overnight, in the dark and then filtered. The filtrate is concentrated to 60 ml and refiltered. This filtrate is concentrated to 20 ml, then refrigerated for 1.5 hours, the solid collected, washed with water and ethanol, and dried, giving 2.3 g of the desired product.

We claim:

1. A compound selected from those of the formulae:

wherein A is selected from the group consisting of O, $SO_2$, N-[alkyl($C_1$-$C_5$)]

n and n' are integers 1–3; L and L' are selected from the group consisting of halide, nitrate, sulfate and an organic monobasic carboxylate; L and L' taken together are ascorbate or a dibasic carboxylate selected from the group consisting of those of the formulae:

(where B is O, $SO_2$ or N—[alkyl($C_1$-$C_5$)], ($CH_2$)m (where m = 1–3), ($CH_2$)m (where m = 2–6),

CHOH,

CH—$CH_3$ and

CH—NHCOCH$_2$—P(=O)(OH)$_2$;

or L and

L' taken together may be a tribasic carboxylate selected from the group consisting of those of the formulae:

-continued

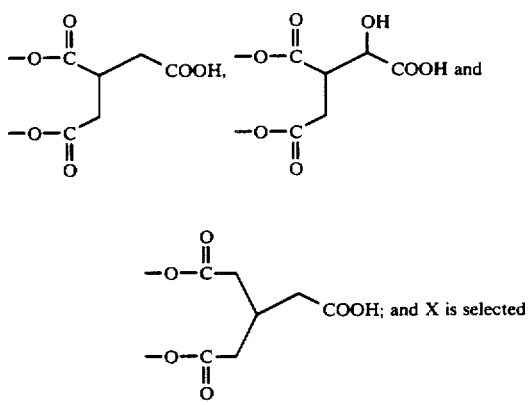

from the group consisting of halogen and hydroxy.

2. The compound according to claim 1, dichloro(-trans-tetrahydro-3,4-furandiamine-N-N')-platinum.

3. The compound according to claim 2, [1,1-cyclobutanedicarboxylato(2-)-O,O¹](racemic)-tetrahydro-3,4-furandiamine-N,N')platinum.

4. The compound according to claim 2, [propanedioato(2-)-O¹,O³](trans(racemic)tetrahydro—3,4-furandiamine-N,N')platinum.

5. The compound according to claim 2, tetrachloro(-trans(racemic)tetrahydro-3,4-furandiamine-N,N')platinum.

6. The compound according to claim 2, [L-threo-3-hexulosonato(2-)-C²,O⁵ gamma-lactone]-(trans-tetrahydro-3,4-furandiamine-N,N')platinum.

7. The compound according to claim 2, bis[hydroxyacetato(1-)-O¹]trans-tetrahydro-3,4-furandiamine-N,N')platinum.

8. The compound according to claim 2, dichloro(-trans-tetrahydro-3,4-thiophenediamine 1,1-dioxide-N,N')platinum.

9. The compound according to claim 2, [1,1-cyclobutanedicarboxylate(2-)-O,O¹](trans-tetrahydro-3,4-thiophenediamine-1,1-dioxide-N,N')-platinum.

10. The compound according to claim 2, dichloro(cis-tetrahydro-2H-pyran-3,4-diamine-N,N')-platinum.

11. The compound according to claim 2, [1,1-cyclobutanedicarboxylato-(2-)-O,O¹](cis-tetrahydro-2H-pyran-3,4-diamine-N,N')platinum.

12. A composition of matter in dosage unit form comprising from about 1 mg to about 1.2 g per square meter of mammalian body surface area of a compound of claim 2, in association with a pharmaceutically acceptable carrier.

* * * * *

UNITED STATES PATENT OFFICE
CERTIFICATE OF CORRECTION

Patent No. 4,716,157  Dated December 29, 1987

Inventor(s) Panayota Bitha et al.

It is certified that error appears in the above-identified patent and that said Letters Patent are hereby corrected as shown below:

Claim 1, Column 14, cancel lines 7-11, inclusive.

Claim 1, Column 14, line 18, insert -- and -- before the formula.

Signed and Sealed this

Twenty-eighth Day of June, 1988

Attest:

DONALD J. QUIGG

Attesting Officer  Commissioner of Patents and Trademarks